(12) United States Patent
Fauconet et al.

(10) Patent No.: US 10,815,182 B2
(45) Date of Patent: Oct. 27, 2020

(54) PROCESS FOR PURIFYING (METH)ACRYLIC ACID INCLUDING A DIVIDING-WALL DISTILLATION COLUMN

(71) Applicant: Arkema France, Colombes (FR)

(72) Inventors: Michel Jean Fauconet, Valmont (FR); Serge Tretjak, Roulhing (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/499,887

(22) PCT Filed: Apr. 3, 2018

(86) PCT No.: PCT/FR2018/050826
§ 371 (c)(1),
(2) Date: Oct. 1, 2019

(87) PCT Pub. No.: WO2018/185423
PCT Pub. Date: Oct. 11, 2018

(65) Prior Publication Data
US 2020/0115311 A1  Apr. 16, 2020

(30) Foreign Application Priority Data
Apr. 4, 2017  (FR) .................... 17 52902

(51) Int. Cl.
| | | |
|---|---|---|
| *C07C 51/44* | (2006.01) | |
| *B01D 3/14* | (2006.01) | |
| *B01D 3/34* | (2006.01) | |
| *B01D 9/00* | (2006.01) | |
| *C07C 51/215* | (2006.01) | |
| *C07C 51/25* | (2006.01) | |
| *C07C 51/21* | (2006.01) | |

(52) U.S. Cl.
CPC .............. *C07C 51/44* (2013.01); *B01D 3/141* (2013.01); *B01D 3/34* (2013.01); *B01D 9/004* (2013.01); *C07C 51/21* (2013.01); *C07C 51/215* (2013.01); *C07C 51/252* (2013.01)

(58) Field of Classification Search
CPC ....... C07C 51/44; C07C 51/21; C07C 51/215; C07C 51/252; B01D 3/34; B01D 3/141; B01D 9/004
See application file for complete search history.

(56) References Cited

U.S. PATENT DOCUMENTS

| | | | |
|---|---|---|---|
| 8,426,637 B2 * | 4/2013 | Koestner ................. | C07C 51/43 562/545 |
| 2009/0253934 A1 | 10/2009 | Ho et al. | |

(Continued)

FOREIGN PATENT DOCUMENTS

WO  WO 2008/033687 A2  3/2008

*Primary Examiner* — Yate' K Cutliff
(74) *Attorney, Agent, or Firm* — Lynn B. Morreale (57) ABSTRACT

The invention relates to the use of a column with a separating wall as a purification/finishing column in a (meth)acrylic acid recovery method based on the use of two distillation columns in the absence of external organic solvent. The method according to the invention improves the energy balance for the method while improving the technical quality of the (meth)acrylic acid recovered. The method according to the invention further produces polymer-grade (or glacial) (meth)acrylic acid compatible with the production of high-molecular weight acrylic acid polymers.

16 Claims, 2 Drawing Sheets

(56) References Cited

U.S. PATENT DOCUMENTS

| 2012/0226074 A1 | 9/2012 | Ho et al. |
| 2013/0284586 A1* | 10/2013 | Lee ........................ B01D 3/141 203/99 |
| 2019/0071382 A1 | 3/2019 | Fauconet et al. |

* cited by examiner

PROCESS FOR PURIFYING (METH)ACRYLIC ACID INCLUDING A DIVIDING-WALL DISTILLATION COLUMN

CROSS-REFERENCE TO RELATED APPLICATIONS

This application is a national stage application under 35 U.S.C. § 371 of PCT/FR2018/050826, filed Apr. 3, 2018 which claims benefit to application FR17.52902, filed Apr. 4, 2017.

TECHNICAL FIELD

The present invention relates to the production of (meth) acrylic acid.

It more particularly relates to the use of a column with a separating wall as a purification/finishing column in a (meth) acrylic acid recovery method based on the use of two distillation columns in the absence of external organic solvent. The method according to the invention improves the energy balance for the method while improving the technical quality of the (meth)acrylic acid recovered.

The method according to the invention further directly produces polymer grade (or glacial) (meth)acrylic acid compatible with the production of high molecular weight acrylic acid polymers.

Technical Background and Technical Problem

The method for synthesizing acrylic acid on a large industrial scale, implements a catalytic oxidation reaction of propylene in the presence of oxygen.

This reaction is generally conducted in the gaseous phase, and usually in two steps: the first step is the approximately quantitative oxidation of propylene into an acrolein-rich mixture, and then, in the second step acrolein is selectively oxidized into acrylic acid.

The gaseous mixture from the second step is constituted of, apart from the acrylic acid, untransformed compounds from reagents used or impurities generated during at least one of the 2 reaction steps, i.e.

- light compounds that cannot condense in the temperature and pressure conditions usually used, i.e. essentially: propylene, propane, nitrogen, unconverted oxygen, carbon monoxide and dioxide formed in low quantity by later oxidation;
- light compounds that can condense, i.e. essentially: water, light aldehydes like unconverted acrolein, formaldehyde, glyoxal and acetaldehyde, formic acid, acetic acid, propionic acid,
- heavy compounds: furfuraldehyde, benzaldehyde, maleic acid and anhydride, benzoic acid, 2-butenoic acid, phenol, protoanemonin.

The complexity of the gaseous mixture obtained in this method requires the application of a set of operations to recover the acrylic acid contained in this gaseous effluent and to transform it into an acrylic acid grade compatible with its final use, for example the synthesis of acrylic esters or the production of acrylic acid polymers and/or of acrylic esters.

A new technology for the recovery/purification of acrylic acid has appeared recently, involving a lower number of purification steps and not requiring external organic solvent.

Patent EP 2,066,613, based on this "solvent-free" technology, describes a recovery method for acrylic acid without using external water, nor azeotropic solvent. This method only uses two distillation columns to purify the cooled gaseous reaction mixture: a) a dehydration column, b) and a finishing column (or purification column) fed by a portion of the flow from the bottom of the dehydration column.

According to this method, the cooled gaseous reaction flow is subjected to a dehydration in a first column. The gaseous flow distilled at the top of the column is partially condensed in a condenser, generating a liquid reflux sent to the dehydration column that participates in the absorption/condensation of the acrylic acid, the non-condensed gaseous effluent being sent back at least in part to the reaction and the rest being eliminated.

The flow from the bottom of the dehydration column is partially sent to a second column called a finishing column. The other portion of this liquid flow is sent back through a heat exchanger in the lower part of the dehydration column, thereby forming a recirculation loop. During the purification/finishing step, from the bottom a flow rich in heavy compounds is eliminated, and from the top a distillate comprising water and light by-products is recovered that is condensed then recycled at the foot of the first dehydration column. The liquid flow coming from the foot of the dehydration column and sent to the finishing column, containing (meth)acrylic acid and the light and heavy impurities from the absorption-condensation step, and the liquid flow coming from the top of the finishing column recycled at the bottom of the dehydration column, containing a flow of (meth)acrylic acid enriched in light compounds, form a "recycling loop" between the 2 columns.

A flow of purified acrylic acid is recovered in the form of liquid or vapor, by side draw from the finishing column. The acrylic acid obtained generally has a purity greater than 98.5% by mass and contains less than 0.5% by mass of water and less than 0.4% by mass of acetic acid. Among other impurities still present, heavy compounds such as aldehydes and protoanemonin are particularly found.

The purified acrylic acid can be used as technical-grade acrylic acid without other purification, for example to produce esters, or can be subjected to extra processing by fractionated crystallization to eliminate the residual impurities and to lead to a polymer-grade (also called glacial) acrylic acid quality.

The finishing column that can be used in the method described in document EP 2,066,613 can have any configuration, for example a packed column, a tray column, a column with a separating wall; the packing can be any type, bulk or structured, and the number of theoretical trays is not limited.

The temperature and pressure operating conditions for the finishing column are not critical in this method, and can be determined in accordance with the distillation methods known from the state of the art. However, preferably, the purification column is operated at a pressure lower than atmospheric pressure, allowing operation at relatively low temperatures, thereby avoiding the polymerization of unsaturated products present, and minimizing the formation of heavy by-products.

In spite of the advantages that come from the purification method described in document EP 2,066,613, drawbacks still remain.

For the production of polymers of (meth)acrylic acid or (meth)acrylic acid esters, it is necessary to produce a quality of technical (meth)acrylic acid sufficiently free of certain bothersome impurities. For example, heavy impurities such as furfural, benzaldehyde and protoanemonin are bothersome because they react in the polymerization process. Other light impurities above a certain level, such as acetic acid, may generate volatile organic compounds that remain within the (meth)acrylic acid polymer and make it unfit for use.

Finally during the production of esters by reaction between technical-grade (meth)acrylic acid and an alcohol, impurities having a carboxylic function, such as acetic acid, crotonic acid, or maleic acid or anhydride form impurities that are difficult to remove and can reduce the yields of the esterification reaction by partially consuming the alcohol used during the reaction.

To prevent these problems, it is necessary to use a finishing column with a large number of rectification levels.

Acrylic acid is a product very sensitive to free-radical polymerization, which leads to the formation of insoluble polymers that foul equipment and cause costly installation stoppages for cleaning.

The addition of polymerization inhibitors reduces this parasite reaction, but this solution is not sufficient for continuous production for long periods, particularly when the temperature inside the column or its equipment is too high. What is more, it is generally difficult to distribute the inhibitor on the column's trays or packing because of dead points generated by the structure, which are made difficult to reach because of liquid reflux containing the polymerization inhibitors.

Accordingly, distillation operations for the purification of flows rich in acrylic acid take place under reduced pressure, so as to limit the temperature, and the distillation columns are generally equipped with simple packing, to allow effective distribution of the liquid containing the inhibitors and to prevent the accumulation of polymer precursor germs. Columns with perforated trays are for example used.

Generally, the internals of the columns that reduce the polymerization initiation phenomena generate more losses of load per theoretical tray installed, than more powerful columns that are instead more prone to the formation and accumulation of polymers.

Increasing the number of rectification trays to produce improved technical acrylic acid quality then leads to increased global load loss in the column, which turns into increased temperature loss in the column and worsening sensitivity to polymerization.

Moreover, acrylic acid has the particularity of easily forming Michael addition derivatives, such as 3-acryloxy-propionic acid, also called acrylic acid dimer. These compounds are heavy products that reduce the recovery yield by consuming monomeric acrylic acid.

Like free-radical polymerization, this covalent reaction to form Michael derivatives is greatly favored by temperature. Consequently, the use of columns with a high number of rectification trays to meet the quality requirements of the acrylic acid leads to drawbacks in terms of product loss, which can only be compensated for in part by additional high-temperature cracking of the Michael derivatives to regenerate the acrylic acid monomer.

Accordingly, there is a substantial need to achieve separation while reducing the number of theoretical rectification trays, both to reduce the risk of polymerization and the formation of Michael addition derivative products, since both of these side effects are favored by a higher temperature.

What is more, the removal of light impurities (mainly water and acetic acid) in a solvent-free method such as described in document EP 2,066,613 requires a recycling loop between the 2 columns whose flow rate is large and inversely proportional to the efficacy of the finishing column. Therefore, increasing the recycling flow rate to compensate for insufficient efficacy leads to extra energy consumption.

The inventors have discovered that using a column equipped with a separating wall and using it in specific conditions, like a finishing column in the method of document EP 2,066,613, overcomes the previously cited drawbacks by leading to a significant energy gain during the purification of the acrylic acid while producing a better quality of technical acrylic acid.

When a distillation column is equipped with a separating wall, the wall being connected with the upper dome of the column in the top portion, and not connected with the bottom of the column in the lower portion, the column includes two sections of which the lower space communicates with the space at the bottom of the column and of which the headspace is separated into two sealed areas.

When the finishing column has this configuration, the inventors have discovered that the light compounds and water contained in the feed flow of the finishing column are removed more effectively from the feed section, and can be recycled at the bottom of the dehydration column in a lower flow rate recycling loop, while allowing the extraction of acrylic acid with improved purity at the top of the other section; and the flow of heavy products forming in the column's lower space is removed at the bottom of the finishing column.

The inventors have also discovered that in this configuration, when a chemical processing agent for the residual aldehydes is added upstream or in the column with a separating wall, it is possible to recover at the top of this column a polymer-grade acrylic acid, this polymer-grade acrylic acid being of superior quality, in particular as regards the residual water, acetic acid and protoanemonin content.

The inventors have also discovered that in some conditions of use of the column with a separating wall, a polymer-grade acrylic acid, meeting specifications for the residual content of aldehydes such as furfural or benzaldehyde, and of protoanemonin can be drawn off directly at the top of the column.

Using a column with a separating wall as a finishing column with the presence of a chemical processing agent for the residual aldehydes, in a recovery method for polymer-grade acrylic acid, has already been suggested in patent application WO 2017/060583 in the name of the Applicant.

In this method, the separating wall of the finishing column is not connected with the upper part of the column. The finishing column is fed at the top from one side of the wall by the flow from the bottom of the dehydration column, and a flow of polymer-grade acrylic acid is obtained at the side draw in the section located on the other side of the separating wall. On the side of the separating wall fed by the flow of acrylic acid to be purified, i.e. in the feed section, the light compounds (mainly acetic acid and water) are removed, and the residual flow flowing back to the bottom of the column containing the acrylic acid enriched in heavy compounds (including the products of reaction with the chemical agent) is distilled in the draw-off section located on the other side of the separating wall.

The purified acrylic acid is collected at a side draw in this second section. The gaseous flow obtained at the top of this draw-off section is mixed with the gaseous flow including the light compounds removed at the top of the feed section, then sent back in liquid form, after condensation, in the recirculation loop at the bottom of the dehydration column. The liquid flow from the bottom of the dehydration column feeding the finishing column and the flow from the top of the finishing column recycled to the dehydration column form a recycling loop containing mainly acrylic acid.

The acrylic acid obtained according to this method is polymer grade, having an acrylic acid content >99%, preferably >99.5%, and including a total aldehyde content <10 ppm, even <3 ppm. It further contains less than 5 ppm of protoanemonin.

In the purification diagram described in patent application WO 2017/060583, to obtain an acrylic acid flow sufficiently free of water and acetic acid, it is necessary to maintain a sufficient flow rate for the flow from the top enriched in light compounds from the finishing column to the dehydration column. This flow from the top is mainly constituted of acrylic acid that we want to recover in entirety. The recycling of a substantial flow from the top of the finishing column to the dehydration column is accompanied by an increased flow rate feed from the bottom of the dehydration column to the feed of the finishing column. Consequently, it is the flow rate of the entire recycling loop that is impacted, and it is necessary to have sufficient energy to ensure the vaporization of the recycling loop. In these conditions only, it is possible to prevent "polluting" acrylic acid with light compounds from the side draw and to guarantee a constant polymer-grade acrylic acid quality.

Moreover, the chemical agents used to remove the aldehydes are not reactive enough to remove the protoanemonin impurity, which is a heavy lactone-type compound. To completely remove the protoanemonin to very low levels, to obtain a glacial (meth)acrylic acid quality compatible with the production of high molecular mass polymers, requires a very high column efficacy. The presence of protoanemonin in polymer-grade acrylic acid, even at a concentration as low as 5 ppm, even 3 ppm, can be totally unacceptable for the production of high molecular mass acrylic acid polymers or acrylic acid salts.

The elimination of protoanemonin remains an unsolved problem in this method. Indeed, obtaining purified product from a side draw, i.e. at a point located lower than the top of the drawing off section, reduces the height of the separation section located below this drawing off.

Consequently, to obtain an acrylic acid flow totally free of protoanemonin, it is necessary to install a very high efficacy column. The drawbacks generated are the cost of investment, an increase in the formation of 3-acryloxypropionic acid (dimer AA) and a risk of increased polymerization, since the addition of rectification trays for a distillation column causes an increase in the loss of total load of the column and consequently an increase in the temperature at the base of the column.

Therefore, a need remains to improve the removal of the protoanemonin impurity in methods for the recovery of polymer-grade acrylic acid described in the prior art.

It has now been discovered that a finishing column equipped with a separating wall used in specific conditions, meets this need, and leads to a polymer-grade acrylic acid including less than 2 ppm of protoanemonin, a water content by mass less than 0.1% and an aldehyde content by mass less than 3 ppm.

DESCRIPTION OF THE INVENTION

The present invention relates to a method for recovering purified (meth)acrylic acid, in the absence of organic solvent, from a gaseous reaction mixture comprising (meth) acrylic acid obtained by gaseous phase oxidation of a (meth)acrylic acid precursor, comprising at least the following steps:

a) the gaseous reaction mixture is subjected to a dehydration without using an azeotropic solvent in a first distillation column called a dehydration column, leading to a flow from the top of which at least part is condensed and sent back to the dehydration column in the form of reflux, and to a flow from the bottom of which at least part is sent back as reflux into the lower part of the dehydration column to form a recirculation loop;

b) the flow from the bottom of the dehydration column is sent at least in part into a second distillation column called a finishing column, which can separate a flow from the bottom containing heavy compounds and a flow from the top containing light compounds, of which at least part is sent back to the dehydration column;

said method being characterized in that:

i) the finishing column is equipped with a separating wall, the wall being connected with the upper done of the column in the top portion and not connected with the bottom of the column in the lower portion, thereby separating the column into two sections equipped with internal distillation elements that ensure gas-liquid contact, of which the lower space communicates with the space at the bottom of the column, and of which the headspace is separated into two sealed areas, said column being fed from a single side of the separating wall, and ii) a gaseous flow rich in light compounds and comprising water and acetic acid is extracted at the top of the feed section, then recycled, after condensation, at least in part in the recirculation loop at the bottom of the dehydration column, and iii) a flow of purified (meth)acrylic acid extracted in gaseous form from the finishing column at the top of the section located on the other side of the feed section, is drawn off after condensation, part of the condensed flow being sent back as liquid reflux at the top of the draw-off section.

For the sake of simplification in the rest of the description of the invention, "feed section" is understood to mean the section of the column with a separating wall that is fed by the (meth)acrylic acid flow to be purified; and "draw-off section" is understood to mean the section of the column with a separating wall from where the purified (meth)acrylic acid flow is extracted at the top.

According to a first specific embodiment, the finishing column is fed at the top at the upper tray of the feed section, and optionally, a portion of the gaseous flow, that is extracted at the top of the feed section, is sent back after condensation, into the feed flow of the finishing column.

According to a second specific embodiment, the finishing column is fed at a point located lower than the upper tray of the feed section, and a portion of the gaseous flow that is extracted at the top of the feed section, is sent back after condensation as liquid reflux at the top of the feed section.

According to these two embodiments, the method according to the invention can produce a purified (meth)acrylic acid flow with better quality, while reducing the flow rate of the recycling loop composed of the bottom of the dehydration column and the top of the finishing column, and therefore reducing the associated energy.

The purified (meth)acrylic acid flow extracted at the top of the finishing column can be used directly as technical-grade (meth)acrylic acid without other purification.

Specifically, technical-grade (meth)acrylic acid advantageously has the following contents by mass of impurities:

Water. <0.2%, preferably <0.05%, more preferably <0.01%

Acetic acid: <0.2%, preferably <0.05%, more preferably <0.02%

Furfural: <0.05%, preferably <0.02%, more preferably <0.005%

Benzaldehyde: <0.05%, preferably <0.02%, more preferably <0.005%

Protoanemonin: <0.05%, preferably <0.02%, more preferably <0.005%.

This technical acrylic acid can be subjected to another process by fractionated crystallization, or by distillation optionally in the presence of a compound reacting with the residual aldehydes, leading to a polymer-grade (meth) acrylic acid quality. Because of the improved technical quality compared with the methods of the prior art, the extra purification to produce a polymer grade is simplified.

The method according to the invention may further comprise the introduction into the finishing column, of a chemical processing agent aiming to reduce the residual aldehyde content, the (meth)acrylic acid flow extracted from the top of the finishing column then being a polymer-grade (meth) acrylic acid flow.

According to certain specific embodiments, the method according to the invention leading to a polymer-grade (meth)acrylic acid can also have at least one of the advantageous characteristics set out below:
- the chemical processing agent is introduced into the feed flow of the finishing column;
- the chemical processing agent is introduced by means of mixing device comprising at least a capacity ensuring the effective dispersion of the chemical agent with the feed flow;
- the chemical processing agent is introduced directly into the finishing column at a point located between the top and the bottom of the column, lower than the tray where the column is fed, preferably, at a point located between about one and two thirds of the height of the feeding section of the finishing column.
- a side draw of a gaseous flow comprising (meth)acrylic acid with intermediate quality is made from the draw-off section.

As an alternative, by adapting the number of trays of the column with a separating wall, in particular a number of theoretical trays ranging from 15 to 20 for each of the feed and draw-off sections, it is possible to directly produce at top of the finishing column a polymer-grade (meth)acrylic acid without falling back on a chemical processing agent for aldehydes.

In all its variants, polymer-grade (meth)acrylic acid drawn off at the top of the finishing column, has a content by weight of (meth)acrylic acid>99.5%, and includes less than 2 ppm of protoanemonin, preferably less than 1 ppm of protoanemonin, and less than 3 ppm preferably less than 1 ppm of total aldehydes (furfural and benzaldehyde). The water content by mass is generally less than 0.05%, preferably less than 0.01%, the acetic acid content by mass is generally less than 0.05%, preferably less than 0.02%.

Another object of the invention is a method for producing purified (meth)acrylic acid comprising at least the following steps:

A) at least one (meth)acrylic acid precursor is subjected to an oxidation in gaseous phase to form a gaseous reaction mixture comprising (meth)acrylic acid;

B) the gaseous reaction mixture is cooled;

C) the cooled gaseous reaction mixture is subjected to the (meth)acrylic acid recovery method as previously defined.

The method according to the invention may further comprise other preliminary, intermediate or subsequent steps as long as they do not negatively affect the production of purified (meth)acrylic acid.

According to one embodiment of the invention, the (meth)acrylic acid precursor is acrolein.

According to one embodiment of the invention, the acrolein is obtained by the oxidation of propylene or by the oxydehydrogenation of propane.

According to one embodiment of the invention, the (meth)acrylic acid precursor is methacrolein.

According to one embodiment of the invention, the methacrolein is obtained by the oxidation of isobutylene and/or of tert-butanol.

According to one embodiment of the invention, the methacrolein is obtained from the oxydehydrogenation of butane and/or isobutane.

According to one embodiment of the invention, the gaseous reaction mixture comprising (meth)acrylic acid obtained by the gaseous phase oxidation of a (meth)acrylic acid precursor comprises carbon from a renewable source.

According to one embodiment of the invention, the (meth)acrylic acid precursor is derived from glycerol, 3-hydroxypropionic acid or 2-hydroxypropionic acid (lactic acid).

According to a preferred embodiment of the invention, the gaseous reaction mixture comprises the acrylic acid derivative of propylene obtained according to a two-step oxidation method.

In an embodiment using an agent for processing residual aldehydes, the method according to the invention produces a flow of polymer-grade (meth)acrylic acid, corresponding to a higher quality to produce high molecular weight polymers, that can be used for example as superabsorbents.

In a preferred embodiment, the method according to the invention produces a polymer-grade (meth)acrylic acid flow without falling back on an agent for processing residual aldehydes.

The method according to the invention does not require the use of an external organic solvent to remove the water contained in the gaseous reaction mixture comprising (meth) acrylic acid. It does not require extra processing by crystallization, costly in energy.

The method according to the invention only uses a dehydration column and a finishing column that may optionally include a step for processing aldehydes using a chemical agent, conducted inside a finishing column including a separating wall in a specific configuration. The physical separation via the separating wall, between the feed flow and the purified acid leads to an increased number of theoretical levels, for a fixed finishing column height and assembly of internal distillation elements, first to effectively separate the light compounds and to obtain an energy gain for recycling, secondly to effectively separate the heavy compounds and to obtain a better quality purified (meth)acrylic acid.

The result is also a reduced quantity of chemical agent necessary to remove the residual aldehydes that are separated more effectively in the finishing column, and even an effective removal of residual aldehydes without needing to use a chemical agent.

According to the invention, it is possible to guarantee a constant quality of polymer-grade acrylic acid with optimized purification cost.

DESCRIPTION OF THE DRAWINGS

Other features and benefits of the invention will appear after reading the detailed description that follows, with reference to appended FIGS. 1 to 4 that show.

DETAILED DESCRIPTION OF THE INVENTION

In the present invention, the term "(meth)acrylic" means "acrylic" or "methacrylic." In the interest of simplification, the rest of the description will make reference to the production of acrylic acid, but also applies by analogy to the production of methacrylic acid.

The term "external organic solvent" denotes any organic compound in which (meth)acrylic acid is soluble and whose origin is external to the method, used as an absorption, extraction or azeotropic distillation solvent.

The term "azeotropic solvent" denotes any organic solvent having the property of forming an azeotropic mixture with water.

The term "that cannot condense" or "uncondensable" denotes compounds whose boiling point is lower than 20° C. at atmospheric pressure.

The term "light," qualifying the by-product compounds, denotes compounds whose boiling point is lower than that of (meth)acrylic acid at the working pressure considered, and by analogy, the term "heavy" denotes compounds whose boiling point is greater than that of (meth)acrylic acid.

The term "chemical processing agent for aldehydes" means a chemical compound that with the aldehydes forms reaction products that are heavier and that are more easily separated from (meth)acrylic acid by distillation, thereby reducing to a very low level the aldehyde content present in the medium to be processed.

"Chemical processing" is understood to mean processing conducted using the chemical processing agent for aldehydes.

This type of processing and the compounds that can be used are well known in the state of the art, without the reactions or complexations used being completely identified. The mode of action essentially aims to form heavier reaction products than the aldehydes to be processed.

This term chemical processing agent for aldehydes excludes polymerization inhibitors which, even though they may have a minor effect on aldehydes, are generally added with the single goal of stabilizing the flow containing (meth)acrylic derivatives from polymerization, where these polymerization inhibitors can be added at various levels and/or in various flows of the installation.

The term "polymer grade" and the term "glacial" mean the same thing and indicate that the (meth)acrylic acid meets criteria for high quality that mean it can be used in the production of high molecular weight (meth)acrylic polymers.

"Recycling loop" between the 2 columns is understood to mean the closed loop formed by the liquid flow coming from the bottom of the dehydration column and sent to the finishing column, and by the liquid flow coming from the top of the recycled finishing column at the bottom of the dehydration column.

The invention aims to produce high-purity acrylic acid with optimized purification cost, and is based on using in specific conditions a column equipped with a separating wall as finishing column in a purification method of the prior art involving a lower number of distillation columns and not requiring an external organic solvent.

Figure 1:
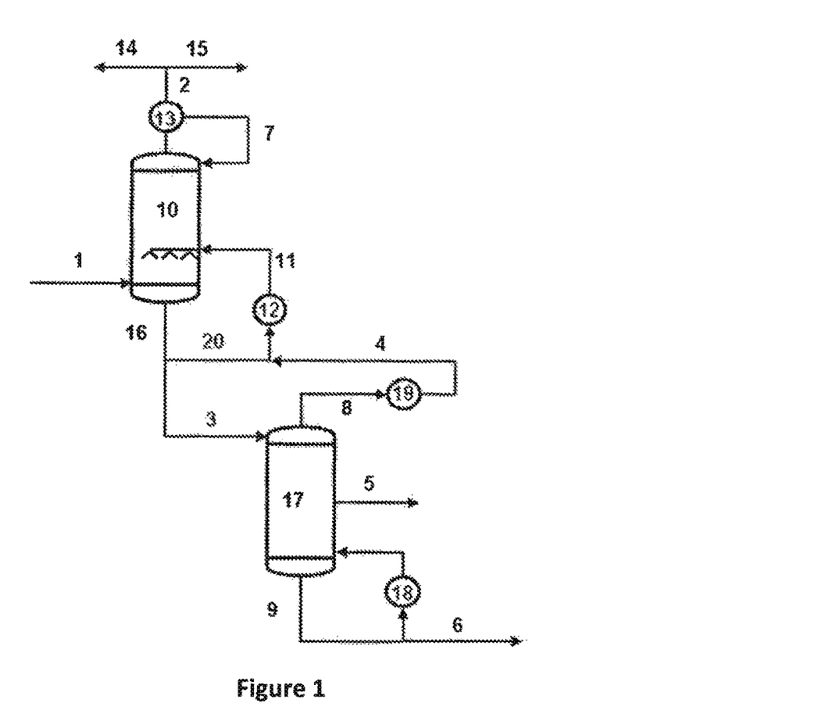
FIG. 1: Installation suitable for the use of the method of the prior art described in patent EP 2,066,613.

According to this method of the prior art shown in FIG. 1, a gaseous reaction mixture 1 comprising acrylic acid obtained by oxidation in the gaseous phase of an acrylic acid precursor feeds a first distillation column 10. The gaseous reaction mixture including a water/acrylic acid ratio by mass generally inclusively between 0.3 and 2, preferably between 0.3 and 1.2, may be previously cooled before being subjected to a dehydration in the dehydration column 10.

The reaction mixture further comprises water and acrylic acid, light products that cannot condense such as nitrogen, oxygen, carbon monoxide and dioxide, and various light or heavy by-products with different chemical natures, which can be light aldehydes like acrolein, formaldehyde, acetaldehyde or glyoxal, heavy aldehydes such as furfualdehyde or benzaldehyde, light acids such as formic acid, acetic acid or propionic acid, heavy acids such as maleic acid, benzoic acid or 2-butenoic acid, and the heavy lactone-type compound protoanemonin.

The dehydration column leads to a top flow 2 of which at least a portion is condensed in a condenser 13 and sent back to the dehydration column in the form of reflux 7 to absorb acrylic acid, the other portion (flow 14 and 15) comprising light compounds that cannot condense being generally sent partially or totally to a purification device or recycled in part towards other steps of the method for producing acrylic acid, preferably in a step upstream of the reactor producing reaction mixture 1.

The entirety of the flow from the top of the dehydration column can be sent to the condenser from the top 13.

The goal of the dehydration step is to eliminate in a flow from the top the bulk of the water present in the reaction mixture, but also the light compounds that cannot condense and light compounds that can condense. It generates a flow from the top 2 comprising the bulk of the water and light compounds, with acrylic acid and the heavy compounds in very low quantities, and a flow from the bottom 16 poor in light compounds comprising almost the entirety of the acrylic acid with heavy by-products, and a content by mass of water generally below 10%, preferably below 7%.

A composition by mass typical of the flow from the bottom 16 of the dehydration column comprises essentially acrylic acid (84-90%), acetic acid (2-10%), water (2-10%), and heavy by-products.

The dehydration column generally comprises from 5 to 50 theoretical trays, preferably from 20 to 30 theoretical trays.

Advantageously, the dehydration column operates at atmospheric pressure or slightly above, up to an absolute pressure of $1.5 \cdot 10^5$ Pa.

Advantageously, the temperature in the upper portion of the dehydration column is at least 40° C., preferably inclusively between 40° C. and 80° C. The temperature of the flow from the bottom of the dehydration column preferably does not exceed 120° C.

The flow from the bottom 16 of the dehydration column is sent at least in part (flow 3), to the top of a second distillation column 17, called a purification column or finishing column, in which are separated a flow from the top 8 and a flow from the bottom 9.

A portion 20 of the liquid flow 16 from the bottom of the dehydration column is sent to a heat exchanger 12 that can be a heater or a cooler and reinjected into the dehydration column, so as to form a recirculation loop at the bottom. Preferably, the portion 11 of the bottom loop is reinjected between the feed of the gaseous reaction mixture and the top of the dehydration column.

The rest (flow 3) of the liquid flow 16 is sent to feed finishing column 17.

The finishing column 17 is generally a classic distillation column comprising from 5 to 30 theoretical trays, preferably from 8 to 20 theoretical trays. This distillation column is associated at the bottom with at least one reboiler 18 and at the top with a condenser 19.

The temperature and pressure in column 17 are not critical, and can be determined in accordance to the distillation methods known from the state of the art. However, preferably, the finishing column 17 operates at a pressure lower than atmospheric pressure, allowing operation at relatively low temperatures, thereby avoiding the polymerization of unsaturated products present, and minimizing the formation of heavy by-products.

Advantageously, the finishing column operates under an absolute pressure ranging from 5 kPa to about 60 kPa, the temperature of the flow from the top being advantageously inclusively between 40° C. and about 90° C., and the temperature of the flow from the bottom being inclusively between 60° C. and 120° C.

The gaseous flow from the top 8 of the finishing column is sent to condenser 19, and the exiting liquid flow 4 is sent back to the dehydration column, mixed with the flow of the bottom loop of the dehydration column. The top flow 8 comprises essentially water and light by-product compounds that can condense.

The flow 9 separated at the bottom of the finishing column comprises the bulk of the heavy by-products, in particular products of Michael addition such as 3-acryloxypropionic acid, maleic anhydride/acid, benzoic acid, and polymerization inhibitors. This flow 9 can be partially recycled at the bottom of the finishing column, or used as raw material for preparing acrylic esters (flow 6).

A flow 5 comprising purified acrylic acid in liquid or vapor form, preferably gaseous, is extracted from the finishing column by side draw. This flow 5 corresponds to technical-grade acrylic acid.

Figure 2:
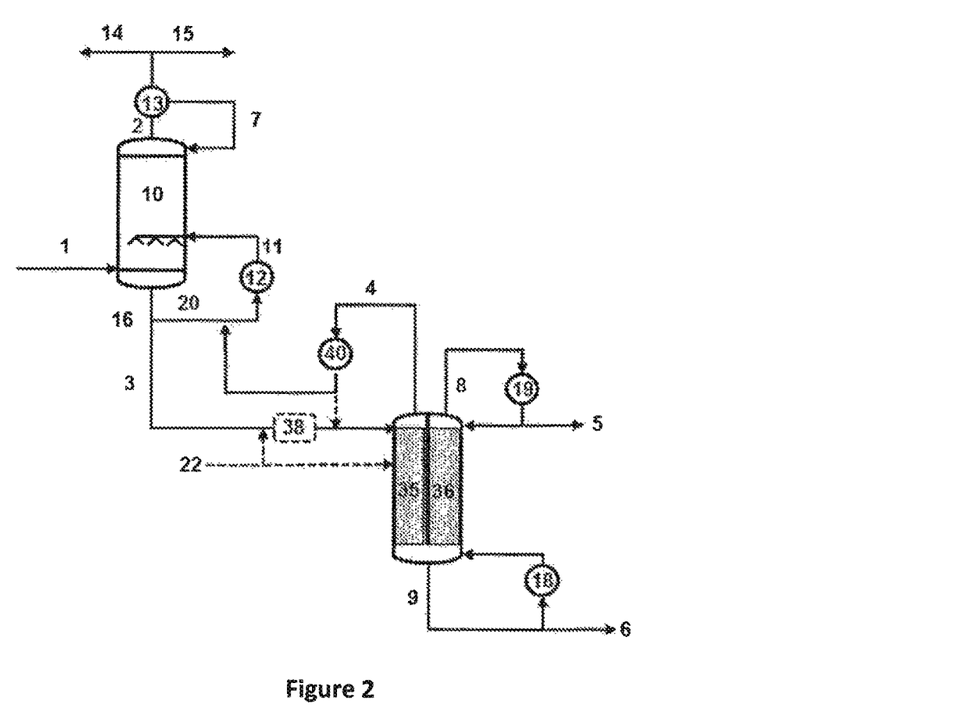
FIG. 2: Installation suitable for the use of the method for recovering purified (meth)acrylic acid according to a first embodiment of the invention, with the optional addition of a chemical processing agent.

FIG. 2 shows an installation suitable for the use of the method for recovering purified (meth)acrylic acid according to a first embodiment of the invention.

This installation is differentiated from the installation of the prior art in that it comprises as finishing column 17, a column equipped with a separating wall, the wall being connected with the upper dome of the column at the top section and not connected with the bottom of the column at the low portion. Therefore, the wall separates the column into two sections 35 and 36 equipped with rectification elements. The lower space of the column located under the separating wall can be empty or preferably equipped with a few rectification elements (not shown in the figure) communicating with the space at the bottom of the column. The headspace is separated by this wall into two empty, unconnected areas.

The number of theoretical trays necessary for the separation of light compounds, in the feed section 35 is generally inclusively between 5 and 20, preferably between 15 and 20, and the lower space common to the 2 sections may comprise between 1 and 5 theoretical trays. In draw-off section 36, the number of theoretical trays is generally inclusively between 2 and 20, preferably between 15 and 20 theoretical trays.

According to a preferred embodiment, the number of theoretical trays in each of the feed and draw-off sections is inclusively between 15 and 20, and the common lower space located under the separating wall is equipped with rectification elements representing between 1 and 5 theoretical trays. According to this embodiment, it is not necessary to add a chemical processing agent for aldehydes to recover at the top of the column a polymer-grade acrylic acid.

The sections of the column can be equipped with all types of internals, for example: bulk or ordered packing, trays that are perforated without downcomers or with downcomers like bubble-cap trays, fixed or mobile valve trays, etc.

The finishing column is fed from a single side of the separating wall, in the feed section 35.

The flow of crude acrylic acid 3 obtained at the bottom of the dehydration column 10, is sent to section 35 at the top of the finishing column.

According to this first embodiment, the finishing column is fed at the top at the upper tray of the feed section.

A gaseous flow 4 rich in light compounds and comprising water is extracted at the top of section 35, condensed in an exchanger 40 and recycled at least in part in the recirculation loop at the bottom of the dehydration column, in flow 20.

A portion of flow 4 that is extracted at the top of the feed section, can advantageously be sent back after condensation into the feed flow of the finishing column.

The flow obtained at the bottom of section 35 containing acrylic acid, with light compounds and water removed, is purified in section 36 in order to remove from the bottom a flow 9 rich in heavy compounds. This flow 9 is partially recycled at the bottom of the finishing column, through a reboiler 18, and the extra 6 is drawn off. This drawn off flow (flow 6) contains residual acrylic acid and heavy compounds like Michael addition derivatives (3-acryloxypropionic). In an advantageous manner, it can be sent to a recovery section to recover the acrylic acid, for example by distillation in an evaporator, or by thermal cracking in a high-temperature reactor, to regenerate the monomer from Michael derivatives, or by combining these two types of equipment. In an alternative manner, flow 9 can also be used as a raw material rich in acrylic acid and in heavy products derived from Michael reactions for the synthesis of esters, in particular in conditions conducive to cracking these heavies and to consecutively regenerating the monomer.

Generally, the finishing column with a separating wall will operate under vacuum in a pressure domain ranging from 5 kPa to 60 kPa, (50 mbar to 600 mbar) preferably between 5 and 20 kPa, with a temperature at the top of the column inclusively between 50° C. and 80° C., and a temperature at the bottom of the column inclusively between 85° C. and 120° C. The ratio of the flow rate by mass between the draw off at the top of the column (5) and the flow rate at the bottom (6) is at least 75/25, preferably at least 95/5. Moreover, the ratio by mass of the return flow rate of the flow from the top of the finishing column on the dehydration column (flow 4) over the sum of the flows drawn off at the top (5) and at the bottom of the column (6) is generally inclusively between 1 and 4.

At the top of section 36, a gaseous flow 8 of purified acrylic acid is extracted from the finishing column. A part of this flow, after condensation, has polymerization inhibitors added, and is then sent back as liquid reflux at the top of the draw-off section. The polymerization inhibitors used are in nature and concentration suitable for the use of the technical acrylic acid recovered in this way.

Figure 3:
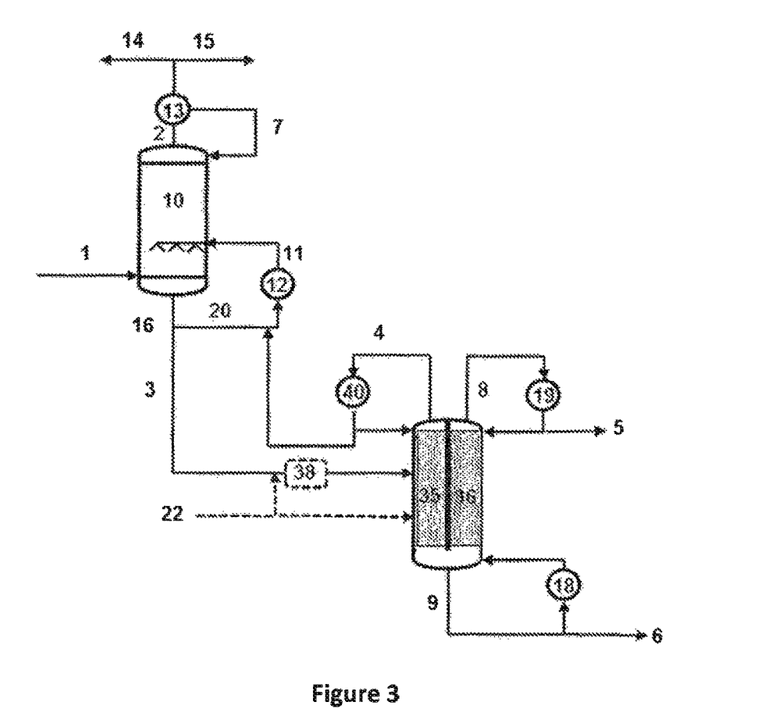
FIG. 3: Installation suitable for the use of the method for recovering purified (meth)acrylic acid according to a second embodiment of the invention, with the optional addition of a chemical processing agent.

FIG. 3 shows an installation suitable for the use of the method for recovering purified (meth)acrylic acid according to a second embodiment of the invention.

According to this second embodiment, the finishing column is fed at a point located lower than the upper tray of the feed section, preferably at a point located between one quarter and three quarters of the height of the feed section and a portion of the gaseous flow 4 that is extracted at the top of the feed section, is sent back after condensation as liquid reflux at the top of the feed section.

In the same way as the first embodiment of the invention, the flow obtained at the bottom of section 35 containing acrylic acid, with light compounds and water removed, is purified in section 36 in order to remove from the bottom a flow 9 rich in heavy compounds. This flow 9 is partially recycled at the bottom of the finishing column, through a reboiler 18, and the extra is drawn off (flow 6), to be sent advantageously to a recovery section for the residual monomer present in free form or combined (3-acryloxypropionic acid), or to a unit for producing acrylic esters, as is described in the first embodiment of the invention.

At the top of section 36, a gaseous flow 8 of purified acrylic acid is extracted from the finishing column. A part of this flow, after condensation, has polymerization inhibitors added, and is then sent back as liquid reflux at the top of the draw-off section. The polymerization inhibitors used are in nature and concentration suitable for the use of the technical acrylic acid recovered in this way.

According to these two embodiments of the invention shown in FIGS. 2 and 3, a device for recovering solids (not shown in the figures), for example a filter, can be placed in line or as a bypass on the recirculation loop at the bottom of the finishing column, to prevent potential fouling of the finishing column.

In comparison with the configuration using a classic finishing column shown in FIG. 1, the invention according to the two embodiments allows the use, for the same number of trays installed, of a shorter column height operating at lower pressure and temperature; it follows that the acrylic acid can be produced reliably and continuously, without interruption caused by the deposit of polymeric solids on equipment. What is more, polymerization inhibitor can be added in a lower quantity to prevent the formation of acrylic acid polymers in the column. Moreover, for a single column height, the invention produces a better quality technical acrylic acid and a reduced flow rate of the recycling loop at the top of the finishing column.

When a chemical processing agent aiming to reduce the residual aldehyde is further added to the finishing column with a separating wall, shown by flow 22, in FIGS. 2 and 3, the purified acrylic acid extracted at the top of the draw-off section 36 corresponds directly to a polymer-grade acrylic acid quality.

The chemical processing agents for aldehydes that can be used in the invention may be those described in the prior art for methods combining a purification by distillation and chemical processing of aldehydes contained in a technical acrylic acid. It may be chemical agents used alone or mixed in any proportions.

In particular, examples are:
amines, such as, for example, without limitation, monoethanolamine, ethylene diamine, glycine, diethylenetriamine, dipropylenetriamine, ortho-, para-, and meta-phenylenediamine;
compounds in the aniline family, such as for example, without limitation, aniline, ortho-, para-, and meta-methylaniline;
compounds in the hydrazine family, such as, without limitation, hydrazine and its salts, hydrazine hydrate, hydrazine sulfate, hydrazine carboxylates, hydrazine hydrochloride, phenylhydrazine, 4-nitrophenylhydrazine, and 2,4-dinitrophenylhydrazine, or also aminoguanidine and its salts, like aminoguanidine hydrogen carbonate;
compounds in the hydrazide family, such as for example, without limitation, carboxylic acid hydrazides and their salts, such as the hydrazides of formic, acetic, propionic, butanoic, pentanoic, maleic acids and the dihydrazides of adipic and succinic acids, urea or urea and hydrazine derivatives, such as semicarbazide or carbohydrazide and their salts;
alone or their mixtures in any proportions.

Preferably, hydrazine or a hydrazine derivative, or an aminoguanidine salt, such as aminoguanidine hydrogen carbonate is used in the invention to reduce the residual aldehyde content.

The chemical agents are added into the flow to be processed, or in solution in a solvent, for example in solution in acrylic acid.

The chemical agent is added in a minimal quantity to obtain a quality of glacial acrylic acid with sufficient aldehyde impurities removed (particularly acrolein, furfuraldehyde and benzaldehyde) to meet the needs of clients. In general, the chemical agent is added in a molar ratio from 0.5 to 10, preferably from 1 to 5, relative to the entirety of the aldehydes present in the medium to be processed.

The chemical agent can be added to the flow that feeds feed section 35, by means of a mixing device 38.

According to this embodiment of the invention (shown in FIG. 2 and FIG. 3), the chemical processing agent for aldehydes with flow 3 is mixed upstream of the finishing column, in a mixing device 38 allowing the most effective dispersion of the chemical processing agent in the flow. This device may in particular contain in series one or more capacities and one or more pieces of equipment for mixing or for heat exchange, so as to achieve the processing at an optimal temperature and transit time. In a non-exhaustive manner, the mixing equipment may include tools generally used by the person skilled in the art to mix liquids, like stirred or recirculated containers or static mixers, but also any type of equipment that allows rapid dispersion of the chemical agent for processing in the flow to be processed, like axial jet mixers, rotary jet mixers, liquid jet ejectors, hydroejectors, pumps, filters, etc.

As an alternative, the chemical processing agent maybe added directly into the finishing column at a point located between the top and the bottom of the column, lower than the tray where the column is fed, preferably, at a point located between about one third and two thirds of the height of the feeding section of the finishing column.

It is indeed necessary, for operation facilities, to limit the risk of formation of solids in an area very close to the bottom of the column, and optionally to place a system allowing for the collection and removal of the solid formed.

What is more, since the light aldehydes are at least partially removed at the top by distillation while penetrating the finishing column operating under reduced pressure, the total aldehyde concentration is lower in the portion located between about one third and two thirds of the feed section of the finishing column, so the quantity of chemical agents to be added is therefore lower, or none.

The flow 9 separated at the bottom of the finishing column is then a flow rich in heavy compounds initially contained in the feed flow 3, or formed during reactions to remove impurities with the chemical agent.

According to the invention, the increase in the number of levels of separation between the feed flow and that allowing the recovery of the polymer-grade acrylic acid, leads to a column with very high efficacy allowing the complete removal of the protoanemonin impurity and also complete removal of aldehyde impurities without requiring processing using a chemical agent.

Figure 4:
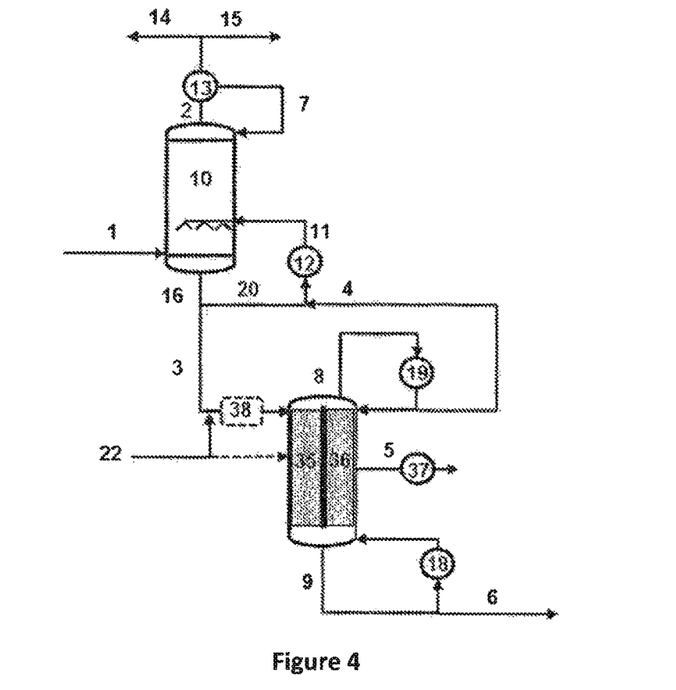
FIG. 4: Installation according to the prior art suitable for the use of a method for recovering polymer-grade (meth) acrylic acid using a distillation column with a separating wall as finishing column.

For comparison, FIG. 4 shows a distillation column with a separating wall as finishing column, in a polymer-grade (meth)acrylic acid recovery method of the prior art.

In this method, the separating wall of the finishing column is not connected with the upper part of the column. The polymer-grade acrylic acid is recovered by side draw from the other side of the feed section.

With this configuration, the chemical agent is injected in the feed flow of the column, or in the feed section of the column, necessarily at a level located above the side draw. The risk of causing the formation of solids that will accumulate in the column is high, and it is not possible to place a system for recovering solids.

The number of levels of separation resulting from the operation of this type of column does not allow the complete removal of the protoanemonin impurity.

Indeed, the separation of acrylic acid with protoanemonin will depend in large part on the number of levels of separation available. In the case of the configuration shown in FIG. 4, section 36 must achieve two operations: i) separating light compounds with the product from the side draw, which can be achieved schematically by the trays inclusively between the upper portion and the position of the side draw of section 36, ii) then separating heavy compounds and acrylic acid between the lower section and the side draw of section 36.

In the method according to the invention, these 2 operations can be respectively achieved by sections 35 and 36 in their entirety.

What is more, the energy related to the flow rate for recycling at the top of this finishing column to the dehydration column to recycle the light compounds and to guarantee constant glacial acrylic acid quality extracted by side draw, remains a drawback in this method of the prior art.

The method according to the invention advantageously overcomes all these drawbacks of the prior art.

The invention will now be illustrated by the following examples, which are not to limit the scope of the invention, defined by the attached claims.

EXPERIMENTAL PART

In the examples, the percentages are indicated in weight for the main compounds unless otherwise indicated, and the following abbreviations were used:
H2O: water
AA: acrylic acid
BZH: benzaldehyde
ACOH: acetic acid
FURF: furfuraldehyde
PTA: protoanemonin Simulations using the ASPEN® software program were used to illustrate the method according to the invention in comparison with the method according to the prior art described in patent EP 2,066,613 B1.

Example 1 (Comparison): Purification Using a Classic Finishing Column with Side Draw The method for recovery and purification of acrylic acid produced by the oxidation in 2 steps of propylene as described in patent EP 2,066,613B1 and shown in FIG. 1, provides at a side draw of the finishing column (17), a flow (5) of purified acrylic acid.

The flow (3) from the bottom of the dehydration column (10) is the feed at the upper tray of the finishing column (17). This column includes a reboiler (18) at the bottom, a condenser (19) at the top and a gas phase side draw (5) that is then condensed in an exchanger (not shown). The finishing column (17) includes 17 theoretical levels, and the side draw is achieved at the level of theoretical tray 13 counted from the top of the column. A portion of the flow at the bottom of the column recirculated through the reboiler (18) is withdrawn (flow 6), and after condensation in the exchanger (19), the gaseous flow (4) from the top of the column is sent back in liquid form into the recirculation loop (20) at the bottom of the dehydration column, Table 1 specifies the main operating conditions of the finishing column (flow rate, temperature, and pressure) and the composition of the various flows:

TABLE 1

| Composition | Feed | Purified product | Bottom of column Flow | Recycled top of column |
|---|---|---|---|---|
| | 3 | 5 | 6 | 4 |
| H2O | 4.43% | <0.01% | <0.001% | 5.86% |
| ACOH | 10.05% | 0.05% | <0.001% | 13.29% |
| AA | 85.01% | 99.81% | 84.18% | 80.62% |
| FURF | 0.0112% | 0.0142% | 0.17% | 0.0052% |
| BZH | 0.0154% | 0.0082% | 0.41% | 0.0049% |
| PTA | 0.0090% | 0.0048% | 0.24% | 0.0028% |
| Flow rate (kg/hr) | 49800 | 11000 | 1195 | 37642 |
| Temperature (° C.) | 62 | 96 | 102 | 74 |
| Pressure (bar) | 0.12 | 0.21 | 0.24 | 0.12 |

The AA quality obtained at the side draw is greater than 99.8% and complies with the expected quality of a "technical"-grade acrylic acid, for the synthesis of acrylic esters for example. For the synthesis of polymers that are even a little demanding in terms of quality (for example for the synthesis of polymers with intermediate molecular weights), this quality is not sufficient, particularly because of the presence of protoanemonin and aldehyde contents that are too high (142 ppm of furfuraldehyde and 82 ppm of benzaldehyde).

This recovery method requires energy consumption of 6.6 Gcal/h to supply the boiler of the finishing column.

Example 2 (According to the Invention):
Purification Using a Finishing Column with a Separating Wall According to an Embodiment of the Invention With reference to FIG. 2, the finishing column is equipped with an inner wall connected to the upper dome, not connected with the base, defining a feed section (35) and a draw-off section (36) that produces the purified quality of acrylic acid at the top. The feed section removes the light compounds recycled at the bottom of the dehydration column after condensation in an exchanger (40).

In this configuration, the feed (35) and draw-off (36) sections each include 14 theoretical trays and the lower draw-off space at the bottom includes 3 theoretical levels.

The distillation of liquid/gas mixtures transiting through each of the sections is ensured by a common exchanger (reboiler 18) at the bottom of the column. The finishing column is fed by the flow from the bottom of the dehydration column (10) to the level of the upper tray of the feed section (35). The flow of purified acrylic acid (5) is drawn off at the top of the draw-off section (36), after condensation of the gaseous mixture in an exchanger (19), and in part sent back in the form of reflux (8) at the top of section (36).

The column with a separating wall is fed by a feed flow (3) unchanged in flow rate and composition compared with that of example 1. In the same way, the flow rates of the recycled lights to the dehydration column (4), of the heavies eliminated at the bottom of the column (6) and of purified product (5) are unchanged compared with those of example 1.

Table 2 specifies the operating conditions of the finishing column (flow rate, temperature, and pressure) and the composition of the various flows:

TABLE 2

| Composition | Feed | Purified product | Bottom of column | Recycled top of column |
|---|---|---|---|---|
| | | | Flow | |
| | 3 | 5 | 6 | 4 |
| H2O | 4.40% | <0.01% | <0.001% | 5.90% |
| ACOH | 10.10% | 0.0119% | <0.001% | 13.30% |
| AA | 85.10% | >99.95% | 89.10% | 80.70% |
| FURF | 0.0112% | 0.0004% | 0.40% | <0.0001% |
| BZH | 0.0154% | <0.0001% | 0.50% | <0.0001% |
| PTA | 0.0090% | <0.0001% | 0.29% | <0.0001% |
| Flow rate (kg/hr) | 49800 | 11000 | 1195 | 37642 |
| Temperature (° C.) | 62 | 82 | 90 | 74 |
| Pressure (bar) | 0.12 | 0.12 | 0.15 | 0.12 |

According to the invention, the technical acrylic acid drawn off from the top of the draw-off section of the column with a separating wall has improved quality relative to that obtained in example 1, particularly for benzaldehyde, furfural and protoanemonin contents.

While not sufficient for the synthesis of polymers using a reaction particularly sensitive to the presence of impurities, particularly aldehydes (for example for the synthesis of high molecular weight polymers), this improved quality of technical acrylic acid can nevertheless be used for some less sensitive applications.

Example 3 (According to the Invention):
Purification Using a Finishing Column with a Separating Wall According to an Embodiment of the Invention Example 2 was reproduced, with identical feed conditions, but with a column with a separating wall including a feed section (35) and a draw-off section (36) each including 17 theoretical trays and a section of space below for drawing off from the bottom including 3 theoretical levels.

Table 3 describes the operating parameters and the compositions of the flows.

TABLE 3

| Composition | Feed<br>3 | Purified product<br>5 | Bottom of column<br>Flow<br>6 | Recycled top of column<br>4 |
|---|---|---|---|---|
| H2O | 4.40% | <0.01% | <0.001% | 5.90% |
| ACOH | 10.10% | <0.01% | <0.001% | 13.30% |
| AA | 85.10% | >99.95% | 89.10% | 80.70% |
| FURF | 0.0112% | <0.0001% | 0.50% | 0.0008% |
| BZH | 0.0154% | <0.0001% | 0.,0% | 0.0008% |
| PTA | 0.0090% | <0.0001% | 0.29% | 0.0005% |
| Flow rate (kg/hr) | 49800 | 11000 | 1158 | 37642 |
| Temperature (° C.) | 62 | 82 | 92 | 74 |
| Pressure (bar) | 0.12 | 0.12 | 0.16 | 0.12 |

In this configuration where each of the sections of the finishing column includes a higher number of trays, the acrylic acid drawn off at the top of the draw-off section has higher purity than that obtained in example 2, and meets the requirements of glacial (or polymer grade) acrylic acid. This quality of acrylic acid can be used directly for the synthesis of the most technical polymers, without falling back on a chemical processing agent that aims to reduce the residual aldehyde content, and without needing extra processing, for example by crystallization or distillation.

In this example, the energy consumption to provide to the finishing column's boiler, is 7.7 GCal/h.

Example 4 (Comparison): Recovery of Glacial Acrylic Acid (Polymer Grade)

By simulation using the ASPEN® software program, the technical acrylic acid obtained by side draw according to the method of the prior art of example 1 must be purified in an extra column including 19 theoretical levels to obtain the same quality of glacial acrylic acid obtained in example 3 according to the method of the invention.

Table 4 indicates the composition of the flows separated from the top and the bottom of the extra column.

TABLE 4

| | Flow | | |
|---|---|---|---|
| Composition | Feed<br>Flow 5 of<br>example 1 | Purified product | Bottom of column |
| ACOH | 0.05% | 0.0608% | 0.0013% |
| AA | 99.80% | 99.90% | 99.90% |
| FURF | 0.0143% | <0.0001% | 0.0783% |
| BZH | 0.0082% | <0.0001% | 0.0453% |
| PTA | 0.0048% | <0.0001% | 0.05% |
| Flow rate (kg/hr) | 11000 | 9000 | 2000 |

For this extra purification, the energy to be used is 5.5 Gcal/h.

The method of the prior art, combining a classic finishing column with the side draw of a flow of technical acrylic acid and an extra distillation column (resulting from the implementation of 17+19, i.e. 36 theoretical levels) requires a total energy provision of 6.6+5.5 Gcal/h, i.e. 12.1 Gcal/h, therefore clearly greater than the energy of 7.7 Gcal/h used in example 3, for equivalent quality of glacial acrylic acid.

The method according to the invention reduces energy consumption by 35% to produce an identical quality of glacial acrylic acid.

The column with a separating wall requires fewer theoretical levels (20 trays on both sides of the wall) to obtain the same quality of glacial acrylic acid. The result is lower investment cost related to the limited height of the finishing column.

This advantage is even greater when perforated trays without a downcomer (dual-flow type) are used, which are generally used for the distillation of particularly heat-sensitive products like acrylic acid (highly increased risks of polymerization when the temperature is higher).

The invention claimed is:

1. A method for recovering purified (meth)acrylic acid, in the absence of organic solvent, from a gaseous reaction mixture comprising (meth)acrylic acid obtained by gaseous phase oxidation of a (meth)acrylic acid precursor, comprising at least the following steps:
    a) subjecting the gaseous reaction mixture to a dehydration without using an azeotropic solvent in a first distillation column called a dehydration column having a top and a bottom, leading to a flow from the dehydration column top of which at least part is condensed and sent back to the dehydration column in the form of reflux, and to a flow from the dehydration column bottom of which at least part is sent back as reflux into a lower part of the dehydration column to form a recirculation loop;
    b) sending at least in part the flow from the bottom of the dehydration column into a second distillation column called a finishing column having a top, a bottom, a top portion, a lower portion, a feed section, and a draw-off section, which separates a flow from the finishing column bottom containing heavy compounds, and a flow from the finishing column top containing light compounds, of which at least part is sent back to the dehydration column;
wherein:
    i) the finishing column is equipped with a separating wall, the wall being connected with an upper dome of the finishing column in the top portion and not connected with the bottom of the finishing column in the lower portion, thereby separating the finishing column into two sections equipped with internal distillation elements that ensure gas-liquid contact, of which a lower space communicates with the space at the bottom of the column, and of which a headspace is separated into two sealed areas, said finishing column being fed in said feed section from a single side of the separating wall, and
    ii) a gaseous flow rich in light compounds and comprising water is extracted at the top of the feed section, then recycled, after condensation, at least in part in a recirculation loop at the bottom of the dehydration column, and iii) a flow of purified (meth)acrylic acid extracted in gaseous form from the finishing column at a top of a section located opposite to the feed section, is drawn off after condensation to form a condensed flow, part of the condensed flow being sent back as liquid reflux at a top of the draw-off section.

2. The method according to claim 1 wherein the (meth)acrylic acid precursor is acrolein, obtained by oxidation of propylene or oxydehydrogenation of propane.

3. The method according to claim 1 wherein the (meth)acrylic acid precursor is methacrolein obtained by oxidation of isobutylene and/or of tert-butanol or from oxydehydrogenation of butane and/or isobutane.

4. The method according to claim 1 wherein the (meth)acrylic acid precursor comprises carbon from a renewable source.

5. The method according to claim 1 wherein the finishing column is fed at a top at an upper tray of the feed section of the finishing column, and optionally, a portion of the gaseous flow that is extracted at the top of the feed section of the finishing column, is sent back after condensation into a feed flow of the finishing column.

6. The method according to claim 1 wherein the finishing column is fed at a point located lower than an upper tray of the feed section of the finishing column, and a portion of the gaseous flow that is extracted at a top of the feed section, is sent back after condensation as liquid reflux at the top of the feed section.

7. The method according to claim 1 wherein the feed section of the finishing column includes a number of theoretical trays inclusively between 5 and 20.

8. The method according to claim 1 wherein the draw-off section of the finishing column includes a number of theoretical trays inclusively between 2 and 20.

9. The method according to claim 1 wherein a lower space of the finishing column located under the separating wall is equipped with rectification elements representing between 1 and 5 theoretical trays.

10. The method according to claim 1 further comprising the introduction into the finishing column, of a chemical processing agent to reduce the residual aldehyde content.

11. The method according to claim 10 wherein the chemical processing agent for aldehydes is chosen from the group consisting of:

monoethanolamine, ethylene diamine, glycine, diethylenetriamine, dipropylenetriamine, ortho-, para-, and meta-phenylenediamine, aniline, ortho-, para-, and meta-methylaniline, hydrazine and its salts, hydrazine hydrate, hydrazine sulfate, hydrazine carboxylates, hydrazine hydrochloride, phenylhydrazine, 4-nitrophenylhydrazine, and 2,4-dinitrophenylhydrazine, aminoguanidine and its salts, aminoguanidine hydrogen carbonate, and carboxylic acid hydrazides and their salts, hydrazides of formic, acetic, propionic, butanoic, pentanoic, maleic acids dihydrazides of adipic and succinic acids, urea and urea and hydrazine derivatives, semicarbazide and carbohydrazide and their salts;

alone or their mixtures in any proportions.

12. The method according to claim 10 wherein the chemical processing agent is introduced into a feed flow of the finishing column.

13. The method according to claim 10 wherein the chemical processing agent is introduced directly into the finishing column at a point located between the top and the bottom of the finishing column, lower than a tray where the column is fed.

14. The method according to claim 10 wherein a side draw of a gaseous flow comprising (meth)acrylic acid with intermediate quality is made from the draw-off section.

15. The method according to claim 1 further comprising an extra processing of purified (meth)acrylic acid by fractionated crystallization, or by distillation optionally in the presence of a compound reacting with residual aldehydes, leading to a polymer-grade (meth)acrylic acid quality.

16. A method for producing purified (meth)acrylic acid comprising the following steps:

A) subjecting at least one (meth)acrylic acid precursor to an oxidation in gaseous phase to form a gaseous reaction mixture comprising (meth)acrylic acid;

B) cooling the gaseous reaction mixture;

C) subjecting the cooled gaseous reaction mixture to the (meth)acrylic acid recovery method as defined according to claim 1.

* * * * *